US00PP28490P2

(12) United States Plant Patent
Van Dijk

(10) Patent No.: US PP28,490 P2
(45) Date of Patent: Oct. 3, 2017

(54) ***ANTHURIUM* PLANT NAMED 'ANTHINEO'**

(50) Latin Name: ***Anthurium andreanum* L.**
Varietal Denomination: ANTHINEO

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 14/999,882

(22) Filed: Jul. 13, 2016

(51) Int. Cl.
*A01H 5/02* (2006.01)

(52) U.S. Cl.
USPC ..... Plt./366

(58) Field of Classification Search
USPC ..... Plt./366
See application file for complete search history.

(56) References Cited

PUBLICATIONS

PLUTO Plant Variety Database Jun. 15, 2017. p. 1.*

* cited by examiner

*Primary Examiner* — Annette Para
(74) *Attorney, Agent, or Firm* — Jondle & Associates, P.C.

(57) ABSTRACT

A new cut flower *Anthurium* plant named 'ANTHINEO' particularly distinguished by having big, shiny, cream, oblong-cordate and durable spathes that retain the original color for a long time, dark green, elliptical cordate, durable leaves, white spadix with green tips, a straight and sturdy peduncle, little shoot formation and a plant height of 150.0 cm to 165.0 cm, is disclosed.

3 Drawing Sheets

Genus and species: *Anthurium andreanum* L.
Variety denomination: 'ANTHINEO'.

BACKGROUND OF THE NEW PLANT

The present invention comprises a new and distinct variety of *Anthurium*, botanically known as *Anthurium andreanum* L., and hereinafter referred to by the variety name 'ANTHINEO'. The new *Anthurium* plant is a product of a planned breeding program conducted by the inventor in Bleiswijk, the Netherlands. The objective of this breeding program was to create a new cut flower *Anthurium* plant with shiny, cream, oblong-cordate and durable spathes.

The new variety originated from a cross-pollination made in August 2000 in Bleiswijk, The Netherlands. The female parent was a white *Anthurium* cut flower plant designated '873-10' (unpatented), and the male parent was a green *Anthurium* cut flower plant designated '2536-01' (unpatented).

A single plant was selected from the progeny of the stated cross in June 2006 and has been asexually reproduced repeatedly by tissue culture in Bleiswijk, The Netherlands over a 10-year period. The present invention has been found to retain its distinctive characteristics through successive asexual propagations.

Plant Breeder's Rights for this variety have been applied for in the European Union on Dec. 4, 2014. 'ANTHINEO' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Shiny, cream, oblong-cordate spathe;
2) White spadix with green tips;
3) Green elliptical cordate leaves;
4) Little shoot formation;
5) Long, straight peduncle; and
6) Tall plant habit.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 282-week old plant grown in a greenhouse in Bleiswijk, The Netherlands in June 2016. Colors in the photographs may differ from the color values cited in the detailed botanical description, which accurately describe the actual colors of the new variety.

DESCRIPTION OF THE NEW VARIETY

Figure 1:
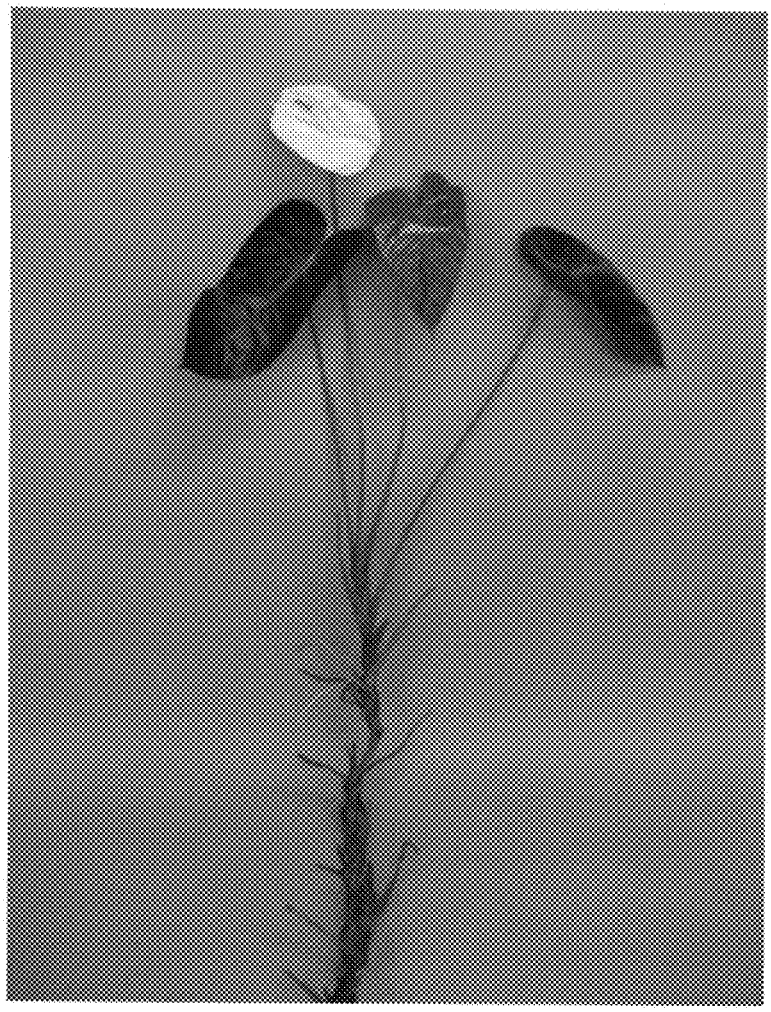
FIG. 1 shows the overall plant habit, including blooms and foliage.
Figure 2:
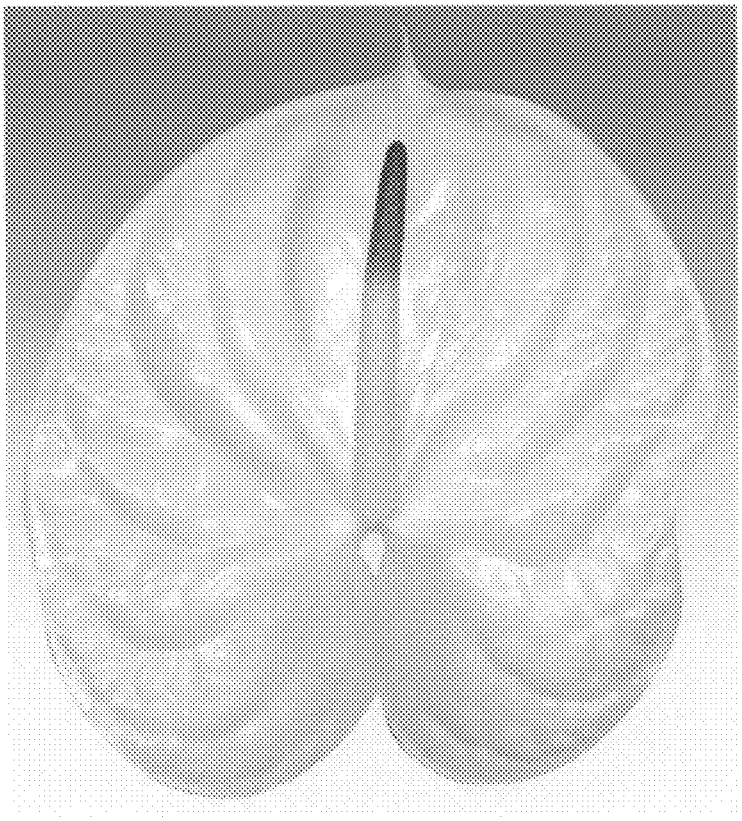
FIG. 2 shows a close-up of the mature spathe.
Figure 3:
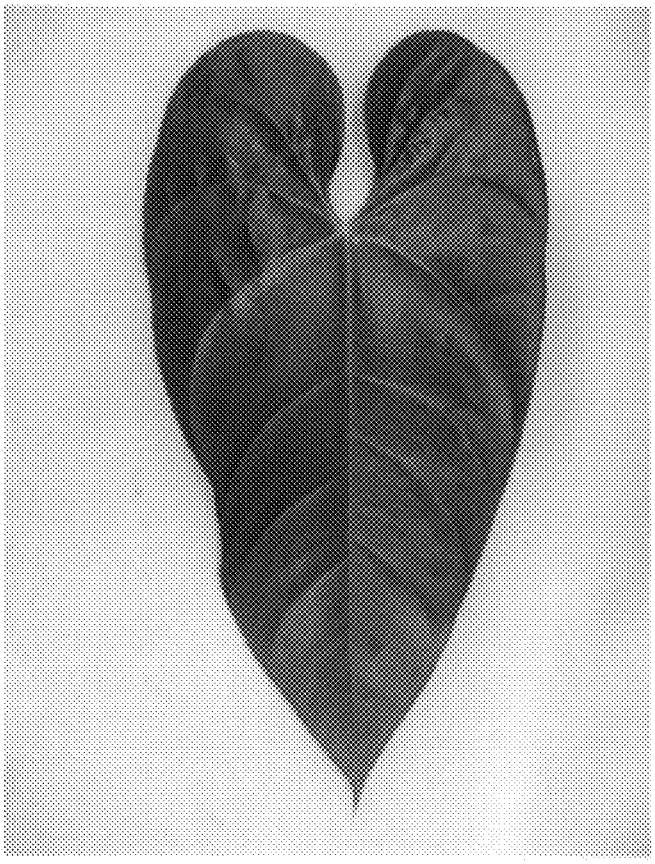
FIG. 3 shows a close-up of the upper leaf blade surface.

The following detailed description sets forth the distinctive characteristics of 'ANTHINEO'. The data which define these characteristics were collected from asexual reproductions carried out in Bleiswijk, The Netherlands. The plant history was taken on 282-week old plants which were planted from tissue culture in 7-centimeter (diameter) pots and grown in a glass greenhouse between 19° C. and 24° C. Observations were made in June 2016. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andreanum* L.

*Common name*.—*Anthurium*.

*Denomination*.—'ANTHINEO'.

Parentage:

*Female parent*.—*Anthurium* plant '873-10' (unpatented).

*Male parent*.—*Anthurium* plant '2536-01' (unpatented).

Plant:

*Propagation*.—Tissue culture (meristem).

*Root description*.—Fleshy-creamy colored roots with small hairy lateral roots having yellow-colored root tips.

*Time to produce a finished flowering plant*.—50 to 70 weeks for a full grown cut flower after planting in a 20 cm (diameter) pot.

*Growth habit*.—Herbaceous perennial.

*Height* (*measured from soil, including inflorescence*) .—150.0 cm to 165.0 cm.

*Width* (*measured from leaf tips*).—70.0 cm to 90.0 cm.

Leaves:

*Immature leaves*.—Length: 26.0 cm to 28.0 cm. Width: 15.0 cm to 17.0 cm. Color: Upper surface: RHS 146A. Lower surface: RHS 146B. Texture (both upper and lower surfaces): Shiny.

*Mature leaves*.—Length (fully expanded): 37.0 cm to 40.0 cm. Width: 19.0 cm to 21.0 cm. Shape: Elliptical cordate. Apex: Acuminate. Base: Cordate. Leaf blade angle with the petiole: Between 70 degrees and 90 degrees. Leaf margin: Entire. Color: Upper surface: RHS 147A. Lower surface: RIIS 146A. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS N144A.

*Lobes*.—Arrangement: Leaf blade has two lobes extending past the petiole. The lobes are non-touching. Length of lobes of mature leaf blades: 8.5 cm to 10.5 cm. Width of lobes of mature leaf blades: 8.0 cm to 10.0 cm. Distance for petiole/leaf junction to highest point on lobes of mature leaf blades: 1.0 cm to 2.0 cm.

*Petiole*.—Cross-section: Round. Diameter: 0.5 cm to 0.7 cm. Length: 50.0 cm to 65.0 cm for a mature leaf size. Color: Mature leaf: RHS 144A. Immature leaf: RHS 144B. Cataphyll color surrounding the petiole: Outside: RHS 144A. Inside: RHS 145B.

*Geniculum*.—Length: 2.0 cm to 2.5 cm. Width: 0.5 cm to 0.6 cm. Color: RHS N144A.

Inflorescence:

*Arrangement*.—Single.

*Flowering habit* (*length of flowering season*).—Continuous.

*Number of inflorescences*.—The plant produces 4 to 6 flowers in the period of one year, but ripe flowers are harvested, so only one flower is present on the plant at a time.

*Fragrance*.—Absent.

*Longevity of the flowers as cut flower*.—35 to 40 days.

Spathe:

*Buds*.—The spathe is tightly rolled around the spadix and extrudes from the peduncle sheath. After the spathe is fully open, the peduncle elongates some extra centimeters.

*Arrangement*.—Spathe angle with the peduncle is between 100 degrees and 120 degrees; the spathe stands on a wiry peduncle about 15.0 cm to 20.0 cm above the foliage.

*Shape*.—Oblong cordate.

*Apex*.—Mucronate.

*Base*.—Cordate.

*Texture*.—Shiny and blistered.

*Margin*.—Entire.

*Size*.—Length: 17.0 cm to 20.0 cm. Width: 14.0 to 16.0 cm.

*Lobes*.—Arrangement: The spathe has two lobes extending past the peduncle. The lobes are overlapping. Length: 6.0 cm to 7.0 cm. Width: 7.0 cm to 9.0 cm.

*Color*.—Just fully open: Upper surface: RHS 157B. Lower surface: RHS 157C. This cream color remains for a very long period, at least more than 35 days after opening.

Peduncle:

*Shape*.—Erect.

*Cross-section*.—Round.

*Length*.—67.0 to 77.0 cm.

*Diameter*.—0.6 cm to 0.8 cm.

*Color*.—RHS 144A.

Flowering time:

*General*.—One small rooted untreated tissue culture plant of 4.0 cm tall will flower, depending on season, after 45 to 54 weeks.

Spadix:

*Size*.—Length: 8.0 cm to 10.0 cm (depending on spathe size). Width (at apex): 0.6 cm to 0.8 cm. Width (at base): 0.8 cm to 1.0 cm.

*Shape*.—Columnar.

*Angle from spadix tip to peduncle*.—120 degrees to 140 degrees.

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS N144A. Mature: RHS 155B. Ages to: RHS 144A.

Flowers:

*Quantity per spadix*.—400 to 500.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 156D.

Reproductive organs:

*Stamens*.—Not visible.

*Pollen amount*.—Absent.

*Pistil*.—Quantity: Many. Length: Less than 0.01 cm. Color: RHS 156D.

*Style*.—Not observed.

*Stigma*.—Shape: Ovoid. Diameter: Less than 0.01 cm. Color: RHS 156D.

*Ovary*.—Rarely visible.

*Ovary color*.—Not measured.

Fruit and seed set: None observed.

COMPARISON WITH PARENTAL AND COMMERCIAL VARIETIES

'ANTHINEO' differs from the female parent plant '873-10' (unpatented) in that 'ANTHINEO' has cream (RHS 157B) spathes, whereas '873-10' has white (RHS NN155C) spathes. Additionally, 'ANTHINEO' has wider spathes and shorter leaves than '873-10'.

'ANTHINEO' differs from the male parent plant '2536-01' (unpatented) in that 'ANTHINEO' has cream (RHS 157B) spathes, whereas '2536-01' has green (RHS 145D) spathes. Additionally, 'ANTHINEO' has wider spathes and shorter leaves than '2536-01'.

'ANTHINEO' differs from commercial variety 'ANTHATCL' (unpatented) in that 'ANTHINEO' has cream (RHS 157B), oblong cordate spathes, whereas 'ANTHATCL' has cream (RHS 4D), cordate spathes. Additionally, 'ANTHINEO' has wider spathes than 'ANTHATCL'.

'ANTHINEO' differs from commercial variety 'ANTHAQUIRE' (unpatented) in that 'ANTHINEO' has cream (RHS 157B), oblong cordate spathes and immature leaves that are green (RHS 146A), whereas 'ANTHAQUIRE' has white (RHS NN155C), cordate spathes and immature leaves that are a mix of green (RHS 146A) and greyed-red-orange (RHS 176D). Additionally, 'ANTHINEO' has an open leaf lobe arrangement, whereas 'ANTHAQUIRE' has a touching to overlapping leaf lobe arrangement.

I claim:

1. A new and distinct variety of *Anthurium* plant named 'ANTHINEO', substantially as illustrated and described herein.

* * * * *